United States Patent [19]
Loftus et al.

[11] Patent Number: 5,832,659
[45] Date of Patent: Nov. 10, 1998

[54] MUSHROOM CAPS WITH REDUCED SCALING

[75] Inventors: Mark Gareth Loftus; Stephen Christopher Lodder, both of Aptos; Erik J. Legg, Capitola, all of Calif.

[73] Assignee: Amycel, Inc., Capitola, Calif.

[21] Appl. No.: 385,909

[22] Filed: Feb. 9, 1995

[51] Int. Cl.$^6$ .............................. A01H 15/00; A01H 1/00
[52] U.S. Cl. ................................ 47/1.1; 47/58; 800/200; 800/220
[58] Field of Search .................... 47/1.1, 58; 800/200, 800/220; 435/172.2; Plt./100

[56] References Cited

U.S. PATENT DOCUMENTS

| | | | |
|---|---|---|---|
| 4,525,368 | 6/1985 | Bengtsson et al. | 426/438 |
| 4,996,390 | 2/1991 | Dahlberg | 800/220 |
| 5,304,721 | 4/1994 | Kerrigan | 800/200 |
| 5,563,317 | 10/1996 | Kerrigan et al. | 800/200 |

FOREIGN PATENT DOCUMENTS

| | | | |
|---|---|---|---|
| WO94/00005 | 1/1994 | WIPO | A01H 1/00 |
| WO94/07357 | 4/1994 | WIPO | A01H 15/00 |

OTHER PUBLICATIONS

Richard W. Kerrigan et al., Mycologia 84(4):575–579, 1992.
Gerda Fritsche, The Mushroom Journal 122:49–53, 1983.
Gerda Fritsche, Genetics and Breeding of Agaricus, Proceedings of the First International Seminar on Mushroom Science, the Netherlands, 14–17 May 1991, pp. 3–18.
T.J. Elliott, Mushroom Science, 8:11–17 (1972).
Richard C. Summerbell et al., Genetics 123:293–300, Oct. 1989.
Richard W. Kerringan, Genetics, 133:225–236, Feb., 1993.
Alan J. Castle et al., Applied and Environmental Microbiology, 54:1643–1648, Jul. 1988.
John G.K. Williams et al., Nucleic Acids Research, 18(22):6531–6535.
M.G. Loftus et al., Theor Appl Genet, 76:712–718 (1988).
William E. Hintz et al., Current Genetics, 9:127–132 (1985).
Alan J. Castle et al., Applied and Environmental Microbiology, 53:816–822, Apr., 1987.
Robert E. Miller, Mycologia, 63:630–634, 1971.
Bernie May et al., Experimental Mycology, 6:283–292 (1982).
Daniel J. Royse et al., Mycologia, 74(4):569–575 (1982).
Daniel J. Royse et al., Mycologia, 74(1):93–102 (1982).
Carlene A. Raper et al., Mycologia, 64:1088–1117 (1972).
Ranjiv S. Khush et al., Applied and Environmental Microbiology, 58:2971–2977, Sep., 1992.
Philippe Callac et al., Mycologia, 85(5):835–851 (1993).
Anton S. Sonnenberg et al., Current Microbiology, 17:285–291 (1988).
John C. Royer et al., Genome, 35:694–698 (1992).
H.J. Evans, Chromosoma, 10:115–135 (1959).
Allen et al., Persistent Meiotic Arrest in basidia of A. bisporus, Mycol. Res., 96(2):125–127, 1992.
Castle et al., RFLPs in the mushrooms *Agarics brunnescens* and *Agaricus bitorquis*. Appl. Environ. Microbiol., 53(4):816–822, 1987.
Fritsche, Breeding *A. bisporus*. The Mushroom Journal, 122:49–53, 1983.
Khush et al., DNA mplification polymorphism of the cultivated mushroom *Agaricus bisporus*. Appl. Environ. Microbiol., 58(9):2971–2977, 1993.
Khush et al., Molecular strategies for Agaricus breeding. The Mycota, II: Genetics and Biotechnology, 321–337, 1995.
Lodder et al., An electrophoretic karyotype of the cultivated mushroom— *Agaricus bisporus*. Current Genetics, 24:496–499 1993.
Loftus et al., DNA polymorphisms in commercial and wild strains of the cultivated mushroom, *Agaricus bisporus*, Theor. Appl. Genet., 76:712–718, 1988.
Smith et al., Comparative studies of the quality of fresh and stored mushrooms of *Agaricus bisporus* with two tropical *Agaricus bitorquis* strains. Annals of Applied Biology, 122(3):593–603, 1993.

*Primary Examiner*—Douglas W. Robinson
*Assistant Examiner*—Melissa L. Kimball
*Attorney, Agent, or Firm*—Cooley Godward LLP

[57] ABSTRACT

*Agaricus bisporus* mushroom strains having characteristics of mushroom strain AA-0028, ATCC accession No. 74325, or a progeny thereof and having improved whiteness over commercial mushrooms of the U1 strain are disclosed along with methods of producing new white mushroom strains.

16 Claims, 1 Drawing Sheet

missing content …

MUSHROOM CAPS WITH REDUCED SCALING

TECHNICAL FIELD

This invention is in the field of mushroom production and is particularly directed to a new strain of mushroom with improved whiteness and shelf-life.

BACKGROUND

The cultivated white button mushroom, *Agaricus bisporus* (Lange) Imbach (syn. *Agaricus brunnescens* Peck), is the predominant mushroom species in cultivation. Breeding progress has been limited over the two centuries that mushrooms have been grown commercially because of the complex and unusual biology of the organism. *A. bisporus* produces predominantly two spores per basidium, in contrast to most basidiomycetes fungi, which produce four spores per basidium. With four spores per basidium, each spore receives one of the four haploid nuclei produced by meiosis and germinates to form a haploid mycelium (a homokaryon). In *A. bisporus* each of the two spores typically receive two post meiotic nuclei referred to as "a" and "b". There is good evidence (Evans H. J., in Chromosoma 10 115–135 (1959)); Summerbell, R. C., Castle, A. J., Horgen, P. A. & Anderson, J. B. in Genetics 123 293–300(1988)) that *A. bisporus* spores derived from two-spored basidia preferentially contain nuclei of complementary mating type. These spores germinate to produce diploid, self-fertile mycelium, known as heterokaryons, which contain the two nuclei a and b. This self fertile heterokaryon can, under the correct environmental conditions, undergo several fruiting cycles commonly referred to as "breaks." A crop of mushrooms comprises the total yield from several successive breaks.

In addition to self fertile spores, viable non-self fertile spores are produced at the rate of 1 to 20%. These homokaryotic spores arise from aberrant three- and four-spored basidia. The homokaryotic mycelium derived from these spores can be used for the controlled crossing that is the foundation of *A. bisporus* breeding. A traditional Agaricus breeding program utilizes the fact that homokaryons grow more slowly than heterokaryons. This permits the screening of large populations of spores for suitable parents, which can then be used in controlled crosses (Kerrigan, R. W., Baller, L. M., Horgen, P. A. & Anderson, J. B), in Mycologia 84 575–579(1992). This approach was used successfully by Fritsche, G. (in The Mushroom Journal 122 49–53 (1983); and in Genetics and breeding of Agaricus, Chapter 1, 3–20, Pudoc (1991)) to develop the strains U1 and U3. Since their release in 1983, these strains have dominated the industry, either as U1, as U3, or as derivatives sold worldwide by numerous spawn companies (Castle, A. J., Horgen, P. A. & Anderson, J. B., in Applied and Environmental Microbiology 53 816–822 (1987); Loftus, M. G., Moore, D. & Elliott, T. J., in Theoretical and Applied Genetics 76 712–718 (1988)).

While U1 has good shelf life, is high yielding under specific growing conditions, and has a good shape, its major drawback is the poor quality of mushrooms from the first break of production. First-break U1 mushrooms are scaly, and the product therefore looks darker in color than is desired for commercial production. Reduced quality of the first break product often dictates that it be sold in the canned mushroom market rather than the fresh market, resulting in significantly reduced profits for the producer. The smoother second- and third-break mushrooms typically make up the bulk of fresh market sales.

The potential impact of mushrooms with a smoother first break of production will depend on the marketplace. In some markets, for example Pennsylvania, mushroom buyers will pressure growers to accept as much as 10 cents a pound less for first-break mushrooms because of their more scaly appearance. Such situations typically occur in periods of overproduction, especially during the summer months. Pennsylvania produces approximately half of the USA's annual production of 754 million pounds (in *Mushrooms*, USDA National Agricultural Statistics Service (1994)); therefore, mushrooms with improved cap smoothness will attract a higher price than conventional U1-type mushrooms under the correct market conditions.

In spite of the difficulties in producing new strains of mushrooms, at least one strain has been the subject of a U.S. plant patent (No. Plant 7,636), while utility patents have issued on specific strains with improved characteristics (e.g., U.S. Pat. Nos. 4,996,390 and 5,304,721).

Accordingly, there is a need for mushroom strains having improved first-break appearance. By the introduction of wild mushroom germ plasm into commercial mushroom strains, we have a developed a novel breeding pedigree. The products of our pedigree give first break mushrooms with less pronounced cap scaling and a more white appearance. A particular advantage of these new hybrid strains is that mushrooms harvested from all breaks of a given crop will be of sufficient quality for sale in the highly profitable fresh market.

BRIEF DESCRIPTION OF THE DRAWING

The invention will be better understood by reference to the following detailed description of specific embodiments when considered in combination with the FIGURE that forms part of this specification, wherein.

SUMMARY OF THE INVENTION

Figure 1:
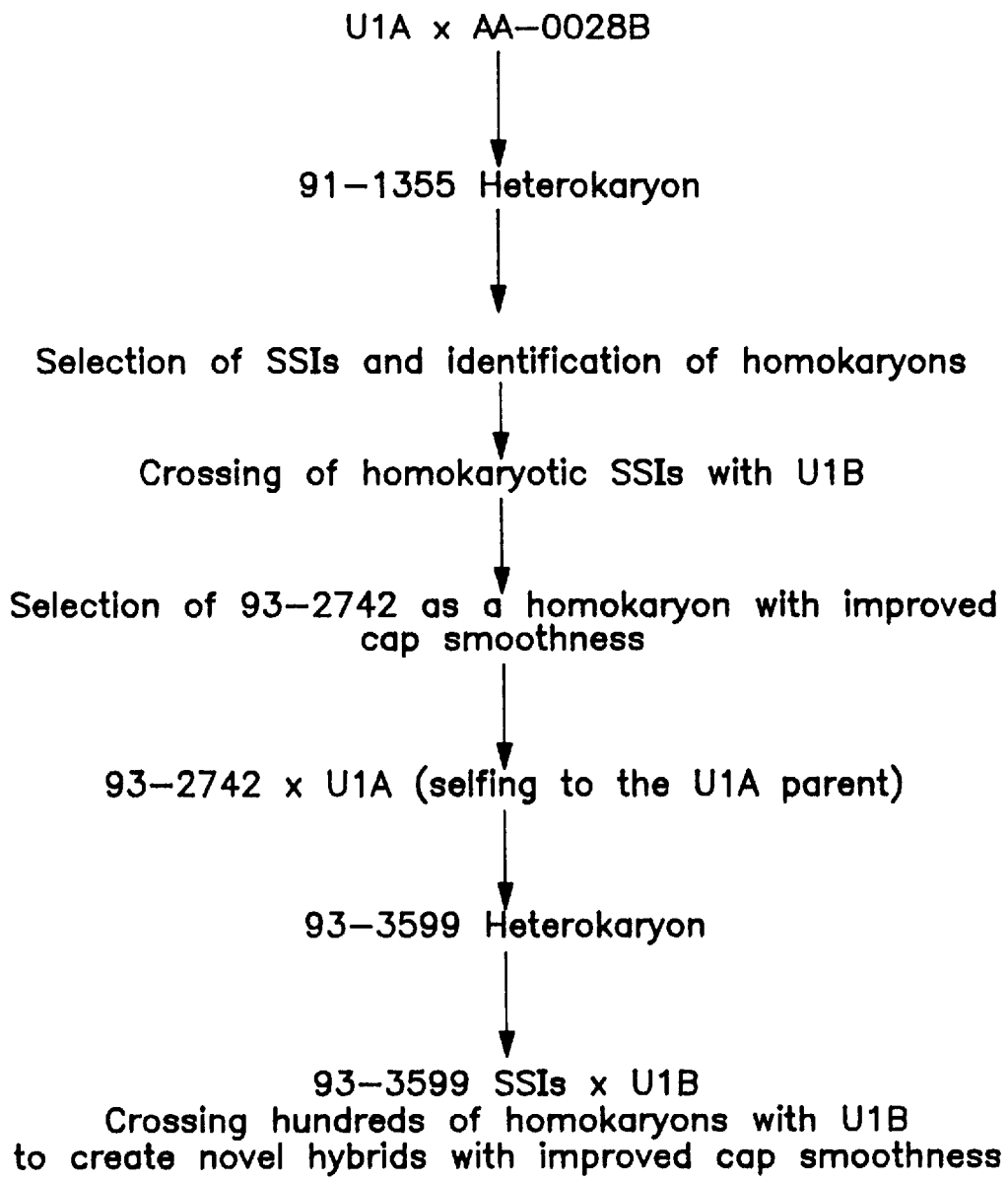
FIG. 1 is a schematic diagram of the breeding program of the invention that lead to the isolation and identification of various strains of improved whiteness.

Accordingly, it is an object of the invention to provide mushroom strains with improved first-break whiteness.

It is another object of the invention to provide mushrooms with acceptable commercial properties in addition to cap whiteness.

These and other objects of the invention have been accomplished by providing an *Agaricus bisporus* mushroom strain having the characteristics of ATCC deposit No. 74325 or a progeny thereof, wherein said strain has a white light reflectance significantly greater than that of strain U1 at a confidence level of at least 95% when measured by a single reflectance measurement technique.

DESCRIPTION OF SPECIFIC EMBODIMENTS

The present invention arose from a specific breeding program that crossed mushrooms from the commercial U1 strain with wild mushroom strains. The specific wild mushroom strain used to obtain the new strains of improved first-break whiteness was obtained from a commercial supplier of wild mushrooms and is identified in the Examples that follow. It is not necessary, however, to reproduce the development program to obtain either the base strain or its progeny, as deposits were made at the American Type Culture Collection, Rockville, Md., USA, on Jan. 26, 1995, which fully enable practice of the invention. As a result of these deposits, anyone can obtain an *Agaricus bisporus* mushroom strain having the characteristics of ATCC accession No. 74324 (inventors' accession number 93-3599) or a progeny thereof, and these strains can be used to obtain mushrooms with improved first-break whiteness, using the technique described herein. Additionally, other progeny of the original wild strain (referred to as AA-0028) can be prepared using the general techniques described here, and these progeny can be selected for the desired whiteness using the techniques described herein.

Methods for the production of mushroom strains, either as direct progeny of a given strain or as a hybrid, are well known. See, for example, U.S. Pat. No. 5,304,721, entitled "Method for the Production of High Proportions of Homokaryons in Breeding Stock of the Mushroom *Agaricus Bisporus*" and U.S. Pat. No. 4,996,390, entitled "Novel Interspecific Mushroom Strains [Agaricus]," as well as numerous publications in the scientific literature, including Sonnenberg et al., "An Efficient Protoplasting/Regeneration System for *Agaricus bisporus* and *Agaricus bitorquis*," *Curr. Microbiol.*, 17:285–291 (1988); May et al., "Confirmation of Crosses Between Lines of *Agaricus brunnescens* by Isozyme Analysis," *Exp. Mycology*, 6:283–292 (1982); Herbraud et al., "Protoplast Production and Regeneration from Mycorrhizal Fungi and Their Use for Isolation and Mutants," *Can. J. Microbiol.*, 34:157–161 (1988); Loftus et al., "DNA Polymorphisms in Commercial and Wild Strains of the Cultivated Mushroom, *Agaricus bisporus*," *Theor. Appl. Genet.*, 76:712–718 (1988); Elliott, "The Genetics and Breeding of Species of Agaricus," in Flegg et al., eds, *The Biology and Technology of the Cultivated Mushroom*, John Wiley and Sons, 1985, pp. 111–139; Castle et al., "Crosses Among Homokaryons from Commercial and Wild-Collected Strains of the Mushroom *Agaricus brunnescens* (=*A. bisporus*)," *Appl. Environ. Microbiol.*, 54:1643–1648 (1988); and Castle et al., "Restriction Fragment Length Polymorphism in the Mushrooms *Agaricus brunnescens* and *Agaricus bitorquis*," *Appl. Environ. Microbiol.*, 53:816–822 (1987). These are merely a few of the numerous publications in the field of mushroom strain production and recognition, and many equivalent publications exist for those who are less familiar with this area of technology and would like to pursue additional background material (see, for example, the publications cited in each of the patent or other publications listed above). However, now that the genetic material of the newly developed strains has been placed in the hands of those skilled in the art of mushroom production by the present invention, one can practice the invention (including the development of progeny strains from the parent deposited strains) simply by using standard mushroom breeding techniques. For example, progeny of the deposited strains can be prepared by following the procedures shown in detail in the Examples that follow.

The breeding plan that resulted in identification of the strains of the invention is outlined in FIG. 1. The aim of the project was originally to determine if wild strains of mushroom could be used to improve commercial strains. Wild heterokaryon AA-0028 (syn. RWK 1551) was chosen because it is very different genetically to current mushroom cultivars (Callac, P., Biliette, C., Imbernon, M. & Kerrigan, R. W., in Mycologia 85 835–851 (1993)) and, in experiments conducted by us, had generally good agronomic characteristics. This point was considered important, because if AA-0028 possessed fewer "bad" genes, it could potentially make back-crossing to re-enforce desired traits a more straightforward task. However, AA-0028 was not selected for appearance and was not itself whiter than U1, but had a cream appearance. It was therefore not apparent before completion of the breeding program that improved whiteness could be obtained, as improved whiteness was an unexpected characteristic of the newly developed mushroom strains in view of the appearance of the parent strains. Only in the latter stages of the breeding program (as detailed below) did smooth, white strains appear from more scaly, cream-colored parents. In order to make possible the preparation of all possible crosses of AA-0028 with U1 strains in accordance with the present invention, strain AA-0028has been deposited under the provisions of the Budapest Treaty with the American Type Culture Collection, Rockville, Md., USA, where it has been assigned accession number 74325.

Homokaryons U1A (our accession number 91-0005), U1B (our accession number 91-0003), AA-0028A, and AA-0028B were crossed in all four wild×cultivated combinations, and the resulting heterokaryons were fruited. The U1A×AA-0028B cross was chosen for further study. This cross was assigned the accession number 91-1355. Mushrooms of this strain came into production three days ahead of U1, and the phenotype was as scaly as the U1control, with a good shape and cream coloration.

One thousand single-spore isolates (SSIs) were collected from a 91-1355 mushroom, and the slowest growing cultures were selected as putative homokaryons. The nuclear constitution of the SSIs were analyzed using random amplified polymorphic DNA (RAPD) markers, and the homokaryotic nature of 72 strains was confirmed.

The homokaryons were then crossed with U1B in order to reconstitute the U1 genome, and the hybrid heterokaryons were fruited. Substantial variation was observed in the first break of production, most notably in cap smoothness. Approximately 25% of the mushrooms had substantially less scaling on the first break of production than the U1 control. The number of crosses was increased to 192, and the smoother capped phenotypes were selected to be re-grown.

After repeat trials, it was observed that, in addition to smoothness, other traits had been inherited from the wild parent. These traits included weak veil, poor shape, and increased susceptibility to bruising. The decision was therefore made to back-cross a selected 91-1355 SSI homokaryon to the U1A parent; such a cross would potentially increase the contribution of desirable traits from U1A and decrease the contribution of undesirable traits from AA-0028B.

The homokaryon selected was 93-2742. When mated with U1B, the resulting heterokaryon (93-2819) produced smooth first-break mushrooms with generally good agronomic traits. The heterokaryon made by back-crossing 93-2742 with U1A was assigned the accession number 93-3599; this is one of two additional strains deposited with the ATCC (accession No. 74324). The second deposited strain is the homokaryon U1B (our accession number 91-0003; ATCC accession No. 74323), which is useful for the production of hybrids as described in the following paragraph.

Spores were germinated from a 93-3599 mushroom, and putative SSI homokaryons were identified on the basis of slow growth rate compared to a 93-3599 control heterokaryon. Slow growing SSIs were crossed with U1B, and the hybrids were fruited. Improved first-break smoothness was observed in approximately 25% of the crosses. The improved crosses are self fertile and can be grown as production mushrooms in the normal manner.

The genetics of the parents of 93-3599 (and thus of 93-3599 itself) have been characterized by restriction fragment length polymorphism (RFLP) analysis and by the random amplified polymorphic DNA (RAPD) technique, both of which are described in more detail in the following Examples. RFLP and RAPD patterns are shown in Tables 1 and 2.

TABLE 1

RFLP Results

| | U1B | U1A | AA-0028B | 93-2742 |
|---|---|---|---|---|
| pAg1n17 | 1.3 | 1.3 | 1.1 | 1.1 |
| pAg1n33 | 3.5/1.5 | 3.5/1.5 | 3.2/1.5 | 3.2/1.5 |
| pAg1n36 | 2.6 | 2.6 | 2.9 | 2.6 |
| pAg1n55 | 2.8 | 2.9 | 6.5 | 2.9 |
| pAg1n147 | 1.7/1.4 | 1.7/1.4 | 1.7/1.0 | 1.7/1.4 |
| pAg1n148 | 4.1 | 4.1 | 1.1 | 1.1 |
| pAg4n6 | 7.0 | 6.0 | 6.0 | 6.0 |
| pAg33n16 | 2.3 | 10.0 | 6.0/1.4 | 6.0/1.4 |

The numbers in the table refer to band size in kilobase pairs (kb) on autoradiographs. Southern blots of Eco RI digested DNA were probed with the DNA clones in the left column.

TABLE 2a

Segregation of RAPD Bands

| Primer* | U1B | U1A | AA-0028B | 93-2742 |
|---|---|---|---|---|
| $A2_{680}$ | − | + | − | + |
| $B7_{520}$ | − | + | − | + |
| $B7_{530}$ | + | − | + | − |
| $B7_{1020}$ | − | + | − | + |
| $B7_{1770}$ | − | − | + | + |
| $B11_{520}$ | − | + | − | + |
| $B11_{1180}$ | − | + | − | + |
| $C20_{1700}$ | − | − | + | + |
| $D1_{980}$ | − | − | + | + |
| $D20_{950}$ | − | − | + | − |
| $E4_{1500}$ | + | − | + | − |
| $E11_{470}$ | − | − | + | + |
| $E16_{840}$ | − | + | − | + |
| $F2_{700}$ | − | − | + | + |
| $F2_{2100}$ | − | + | − | + |
| $F6_{560}$ | − | − | + | + |
| $G4_{580}$ | − | + | − | + |
| $G4_{640}$ | − | − | + | + |
| $G4_{1080}$ | − | − | + | + |
| $G4_{1120}$ | − | − | + | + |
| $G5_{620}$ | − | − | + | + |
| $G6_{1000}$ | − | + | − | + |
| $G6_{1180}$ | − | − | + | + |
| $G8_{540}$ | − | − | + | + |
| $G9_{300}$ | − | + | − | + |
| $G10_{580}$ | − | − | + | + |
| $G11_{1250}$ | − | − | + | + |
| $G12_{1870}$ | − | − | + | + |
| $G13_{920}$ | − | − | + | + |
| $G14_{980}$ | − | − | + | + |
| $G14_{1390}$ | − | − | + | + |
| $G16_{900}$ | − | − | + | + |
| $G16_{1140}$ | − | + | − | + |
| $H1_{910}$ | − | − | + | + |
| $H3_{520}$ | − | − | + | + |
| $H3_{1200}$ | − | − | + | + |
| $H4_{610}$ | − | − | + | + |
| $H5_{1500}$ | − | − | + | + |
| $H6_{1300}$ | − | − | + | + |
| $H15_{360}$ | − | − | + | + |
| $H16_{1200}$ | − | − | + | + |
| $H17_{900}$ | − | − | + | + |
| $H18_{1800}$ | − | − | + | + |
| $H20_{720}$ | − | − | + | + |

*The numbers in subscript refer to band size(kb) of the RAPD fragments. See table 2b. for primer sequences.

TABLE 2b

Primer Sequences for RAPD Analysis

| Primer | Sequence |
|---|---|
| A2 | 5'-TGCCGAGCTG-3' |
| B7 | 5'-GGTGACGCAG-3' |
| B11 | 5'-GTAGACCCGT-3' |
| C20 | 5'-ACTTCGCCAC-3' |
| D1 | 5'-ACCGCGAAGG-3' |
| D20 | 5'-ACCCGGTCAC-3' |
| E4 | 5'-GTGACATGCC-3' |
| E11 | 5'-GAGTCTCAGG-3' |
| E16 | 5'-GGTGACTGTG-3' |
| F2 | 5'-GAGGATCCCT-3' |
| F6 | 5'-GGGAATTCGG-3' |
| G4 | 5'-AGCGTGTCTG-3' |
| G5 | 5'-CTGAGACGGA-3' |
| G6 | 5'-CTGCCTAACC-3' |
| G8 | 5'-TCACGTCCAC-3' |
| G9 | 5'-CTGACGTCAC-3' |
| G10 | 5'-AGGGCCGTCT-3' |
| G11 | 5'-TGCCCGTCGT-3' |
| G12 | 5'-CAGCTCACGA-3' |
| G13 | 5'-CTCTCCGCCA-3' |
| G14 | 5'-GGATGAGACC-3' |
| G16 | 5'-AGCGTCCTCC-3' |
| H1 | 5'-GGTCGGAGAA-3' |
| H3 | 5'-AGACGTCCAC-3' |
| H4 | 5'-GGAAGTCGCC-3' |
| H5 | 5'-AGTCGTCCCC-3' |
| H6 | 5'-ACGCATCGCA-3' |
| H15 | 5'-AATGGCGCAG-3' |
| H16 | 5'-TCTCAGCTGG-3' |
| H17 | 5'-CACTCTCCTC-3' |
| H18 | 5'-GAATCGGCCA-3' |
| H20 | 5'-GGGAGACATC-3' |

Progeny of the deposited strains obtained by crossing a deposited strain with a second mushroom strain are characterized by having at least one RAPD or RFLP band "characteristic" of the deposited strain. Such a "characteristic" band (or DNA fingerprint) is one that is not present as a corresponding RAPD or RFLP band of the second strain. Such characteristic bands of 93-2742 relative to the U1 strain can be seen for RFLP analysis in Table 1 and for RAPD analysis in Table 2. For example, a 1.1 kb fragment is found in strain 93-2742 and not in homokaryons U1B or U1A; this band is therefore characteristic of 93-2742 (relative to U1) and can be used in the process of identifying progeny of strain 93-2742 when crossed with U1. In a similar manner, any of the "H series" primers (H1, H3, H4, H5, H6, H15, H16, H17, H18, or H20) produces a characteristic band ($H1_{910}$, $H3_{520}$, etc., as shown in Table 2a) that can be used to identify a progeny of 93-2742 when crossed with a U1 strain. Other characteristic bands are readily apparent in Tables 1 and 2. Characteristic bands of the AA-0028 strain or of other progeny of AA-0028 are obtained in the same manner.

Characteristic bands identified as shown in the Examples (or by any other technique) for other mushroom strains or species used in a crossing program can be used to help identify progeny of the deposited strains. Generally, the more characteristic bands that are present, the more closely the progeny will resemble the parent. After several crosses, only a few characteristic bands may be present (depending on random reassortment process during meiosis). Preferred strains retain at least 5, preferably at least 10, characteristic RAPD bands or at least 2, preferably at least 5, characteristic RFLP bands. However, any progeny strain that retains the whiteness characteristic of the strains of the invention is considered to remain within the scope of the invention. Such white progeny strains (relative to the U1 standard) can readily be selected by visual inspection after crossing.

In addition to characteristic bands associated with the genetic material of the invention, a mushroom strain obtained by crossing a strain of the invention with another mushroom strain will have RAPD and/or RFLP bands characteristic of the second strain; e.g., the mushroom strain, in addition to having a characteristic RAPD or RPLP band of the invention will have at least one RAPD or RFLP band in common with the second strain (e.g., U3) that is not present as a corresponding RAPD or RFLP band from, e.g., strain 93-2742. These characteristic bands will be useful in identifying the second strain that has been crossed with a parent strain of the invention to give a progeny strain of the invention.

Strains of the invention have caps that are significantly whiter than the most common commercial strain, U1. Whiteness is measured by ability to reflect all wavelengths of visible light. Specific measurement techniques are set forth in detail in the Examples, but other measurement techniques can be used as well, as long as the same technique is used to measure whiteness of both the strain of the invention and the reference U1 strain. A given strain will be sufficiently white to be considered within the scope of the invention when the strain has a white light reflectance significantly greater than that of strain U1 at a confidence level of at least 95% when measured by a single reflectance measurement technique. Statistical analysis is by standard techniques, such as those described in N. M. Downie and R. W. Heath, *Basic Statistical Methods*, Harper & Brothers, New York, 1959 (see especially chapter 12, pp. 123–139, entitled "Testing Difference Between Means"). Strain U1 has a typical reflectance of 73%. Strains of the invention typically have a reflectance of at least 76% (significant difference at 95% confidence level), preferably at least 78%, more preferably at least 80%.

Following the method described herein, a number of lines derived from our pedigree have been identified which have inherited improved first break smoothness, in addition to many of the traits which have made U1 such a good cultivar, such as good cap shape, thick stems, thick veil and a good shelf life.

Additionally, the presence of other traits inherited by the descendants of 93-3599 was also observed. Some of our lines have a more rounded cap shape than U1 and some of our lines are one day earlier into first break than U1. Therefore our breeding program is capable of producing a number of new cultivars, each having improved cap smoothness and a combination of other traits.

Inheritance of Markers

The RFLP data (Table 1) and the RAPD data (Table 2a) clearly show the segregation of markers into 93-2742. We concentrated on finding markers inherited from AA-0028, as these loci are absent from U1 type mushrooms. We also included RFLP and RAPD markers inherited from the U1A parent as this will allow the separation of our pedigree from other breeding programs derived from sibling spores of 93-2742. However, the markers shown in the Examples that follow are not the only markers that can be used to characterize the strains and progeny strains of the invention, and the invention should not be considered limited to the example markers.

Inheritance of Smoothness

A colorimetric study was undertaken to scientifically measure improved cap smoothness. Four hybrids pre-selected for improved cap smoothness were grown alongside U1 and the Y values were measured.

Table 3 clearly shows that the four hybrids we selected for testing had significantly higher Y values than U1. The four hybrids we measured were pre-selected by eye as being smoother than U1, and therefore we had complete agreement with the visual assessment and the scientific measurements.

Novelty of the New Hybrid Strains

The uniqueness of the new hybrids is shown by the RFLP (Table 1) and RAPD (Table 2a) results. Homokaryon 93-2742 is the product of a unique meiotic event and has inherited markers from U1A and AA-0028B. A large number of markers inherited from AA-0028B were identified which allow the separation of the new strains from closely related U1 type mushrooms. When the RFLP and RAPD data are combined, a genetic fingerprint for 93-2742 can be deduced. The DNA fingerprint described in this document contains thirty four RAPD or RFLP loci which are absent from U1, in addition to fourteen markers inherited from U1A. Markers inherited from U1A were included to distinguish hybrids from this breeding program from breeding programs built around siblings of 93-2742.

When 93-2742 is mated with U1A to create the 93-3599 heterokaryon, meiosis will reassort the 34 loci we have defined, and 93-3599 SSI homokaryons will inherit a subset of the markers from Table 1 and Table 2a. According to Mendelian genetics, it would be expected that each locus would segregate in a 1:1 ratio. All 93-3599 SSI derived homokaryons will therefore inherit a different subset of the markers described herein. It is therefore possible to distinguish the new hybrid strains from each other and from U1.

With the final step of crossing the 93-3599 SSIs with U1B, each partial pattern of defined markers will be added to the pattern of U1B. Using the markers described herein, it is therefore possible to predict all marker combinations. A theoretical total number of combinations is 23 (for these markers), assuming that all 34 loci are capable of recombination and reassortment. The real number of combinations will be lower than this number because some of our markers will be on the same chromosome and will therefore be linked. An accurate estimate of the number of possible marker combinations will be possible only when the definitive genetic map of *Agaricus bisporus* is published. However, such a map is not necessary to the practice of the invention.

In addition to the evidence provided by DNA analysis, novelty of our new hybrid strains is demonstrated by the colorimetric study described in Table 3. Four of our new hybrid strains selected as smoother by visual inspection were grown with a U1 control. Mushrooms were fruited under standard U1 conditions, and the "Y" values we measured were significantly higher in our hybrids than in the U1 control.

TABLE 3

Y Value Comparison taken between U1 and four hybrids

| Strain | Mean Y value[a] | Fisher's LSD[b] |
|---|---|---|
| 94-4053 | 80.87 | a |
| 94-4137 | 78.90 | b |
| 94-4077 | 76.33 | c |
| 94-4135 | 76.30 | c |
| U1 | 73.57 | d |

[a]Average of 100 scores
[b]Fisher's Least Significant Difference procedure. Any two means having a common letter are not significantly different at the 5% levle of significance.

EXAMPLES

Strains

Mycelium from commercial strain U1 (material provided by Amycel, San Juan Bautista, Calif. 94045) and from cream-colored wild strain AA-0028 (syn. RWK 1551; material purchased from R. W. Kerrigan, Sylvan Spawn Company, 1163 Cabot Rd., Cabot, Pa. 16023) were used in the development of our breeding lines.

All strains were cultured, maintained, and selected on Compost Lite Agar (CL) at 21° C. CL Agar comprises potato dextrose agar (PDA; Difco) with 0.5% Yeast extract (Sigma) and 10% compost extract. Compost extract was made by infusing equal volumes (w/v) of phase II compost and $H_2O$. The compost and water were autoclaved twice for 90 minutes, and the aqueous extract was added to make CL agar. Mushroom spawn was made using millet grain inoculated with 2 $cm^2$ chunks of colonized CL agar. Spawn was grown for four weeks and was shaken at weekly intervals.

Compost and Media

Heterokaryons were fruited on standard phase II mushroom compost. The compost was colonized with inoculated millet spawn for thirteen to fourteen days, with bed temperatures in the range 21°–27° C., and $CO_2$ between 5000 and 10000 parts per million (ppm). Beds were then covered with a 5-cm layer of casing formulation (approximately 75% peat/25% Ca $CO_3$), and the cased beds were scratched after five days to encourage mycelial growth into the casing layer. Two days after scratching the beds were flushed, with the air temperature dropping to 16° C. and the $CO_2$ dropping to 1000 to 1500 ppm. Mushrooms appeared approximately two weeks after flushing, and during first break bed temperatures were held at 18°–21° C. For nearly every crop, only the first break of production was assessed.

For DNA isolation, cultures were either grown in MPYFE liquid medium (Castle et al., 1987) or on cellophane over CL Agar. Harvested tissue was frozen at 28°–70° C. and was freeze dried prior to DNA isolation.

Derivation and Isolation of Homokaryons

Mycelium from U1 and AA-0028 was protoplasted as described in Khush, R. S., Becker, E. & Wach, M. W. (Applied and Environmental Microbiology 58 2971– 2977 (1992)), and slow growing protoplast regenerants were isolated. DNA was isolated as described in the same Khush et al. publication. In brief, the techniques were as follows.

Cultures (either grown in MPYFE liquid medium or on cellophane over CL Agar) were protoplasted as follows. A 1 mg/ml solution of Novozyme (Novo Biolabs, Denmark) in Protoplast buffer (0.8M $MgSO_4$/20 mM sodium citrate, pH 5.5) was prepared. The solution was mixed and filtered through a 0.2 μm syringe filter unit. Next, colonies of A. bisporus were placed in the protoplasting solution, followed by thorough mixing. The mixture was incubated for two hours at room temperature.

Following incubation, the mixture was filtered through glass wool resting in a microcentrifuge tube. Protoplast density was measured with a hemocytometer slide, and protoplast concentration was adjusted through centrifugation and resuspension in protoplast buffer.

Protoplasts were regenerated on Regeneration Medium (RM: 200 ml compost extract/5 g Peptone(Bacto)/205.4 g sucrose/15 g agar per liter). Protoplasts were spread on plates of fresh RM with a sterile glass rod. Regenerants appeared after 7 day, and we selected for the slow growing types.

DNA was prepared from freeze dried mycelium. First, freeze dried tissue was ground with a glass rod, and 0.6 ml of 65° C. DNA extraction buffer (0.7M sodium chloride/0.1M sodium sulphite/0.1M Tris-HCl, pH 7.5/0.05M EDTA/1% SDS) was added. Tubes were mixed and placed at 65° C. for 30 minutes. Next, 0.6 ml of chloroform:isoamyl alcohol (24:1) was added, and the tubes were mixed. Tubes were placed on ice for 30 minutes, followed by centrifugation at high speed (12000×g) for 30 minutes.

Supernatants were placed in fresh tubes, and 2 volumes of ethanol were added. After mixing, the tubes were centrifuged at low speed (2000×g) for 30 seconds. Pellets were resuspended in 200 μl sterile water, and 100 μl of 7.5M ammonium acetate were added. The tubes were then mixed and placed on ice for 1 hour.

Next, the tubes were spun at high speed (12000×g) for 30 minutes, and the supernatants were transferred to fresh tubes. Isopropanol (0.54 volume) was added, and the tubes were mixed by gentle inversion. Supernatants were removed, and pellets were washed with 70% ethanol. Finally, ethanol was removed through centrifugation and pipetting, and the DNA was resuspended in 100 μl of TE (10 mM Tris-HCl, pH 7.5/1 mM EDTA).

DNA from the protoplast regenerants was analyzed using the Random Amplified Polymorphic DNA technique (RAPDs; in Williams, J. G. K., Kubelik, A. R., Livak, K. J., Rafalski, J. A. & Tingey, S. V., (1990) in Nucleic Acids Research 18 6531–6535). Both homokaryons were identified from each strain, and they were designated U1A, U1B, AA-0028A, and AA-0028B respectively. The RAPD primers used in this study were all purchased from Operon Technologies (Alameda, Calif.). The numbers and sequences are described in Table 2b.

In addition to protoplast-derived homokaryons, spontaneous homokaryons were identified from single spore isolates (SSIs). Spores were collected from mushrooms, and the spores were diluted in $H_2O$ containing 1% Tween 80. Spore density was calculated on a hemocytometer slide, and spore dilutions were plated out on PDA.

DNA Fingerprinting

DNA fingerprinting of novel strains was completed using two methodologies; RFLPs (Restriction Fragment Length Polymorphisms; Botstein, D., White, R. L., Skolnick, M. & Davis, R. W, in the American Journal of Human Genetics 32 314–321(1980)) and RAPDs (Williams et al. (1990).

Eight genomic DNA clones were used For RFLP analysis: pAg1n17, pAg1n33, pAg1n36, p1Agn55, pAg1n147, pAg1n148, pAg4n6 and pAg33n16 (Castle et al. 1987; Summerbell, R. C., Castle, A. J., Horgen, P. A. & Anderson, J. B., in Genetics 123 293–300 (1989)). These probes were applied to Southern blots prepared from Eco RI digested DNA of U1A, U1B, AA-0028B and 93-2742 as described in Khush et al. (1992), cited above.

A total of forty-four RAPD loci were utilized; the primer sequences are 27 shown in Table 2b.

Color Measurements

In order to demonstrate the smoothness of our mushrooms, we completed colorimetric measurements using a Minolta Chroma Meter CR-100. We used the Yxy measuring mode, where Y is a brightness factor expressed as a percentage based on a white surface with a reflectance of 100%. Mushrooms with scaly caps reflect back less light than mushrooms with smooth caps, and therefore the smoother the mushroom, the higher the Y value.

First break mushrooms of cap diameter 2.5–5 cm were collected, and measurements were taken on the sides of the caps at random. The cap sides are where scaling on first break U1 type mushrooms is most pronounced. One hundred Y values were taken per strain and the data was analyzed using Fisher's t test (Minitab Statistical Software, release 8).

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An *Agaricus bisporus* mushroom, wherein said mushroom belongs to or is a progeny of a deposited mushroom strain identified as 93-3599, ATCC accession No. 74324, or AA-0028, ATCC accession No. 74325, and wherein said mushroom has a white light reflectance significantly greater than that of strain U1 at a confidence level of at least 95% when measured by a single reflectance measurement technique.

2. The mushroom of claim 1, wherein said mushroom is a progeny of AA-0028 and has at least one RAPD or RFLP band in common with strain 93-2742 or AA-0028 that is not present as a corresponding RAPD or RFLP band from U1.

3. The mushroom strain of claim 2, wherein said strain is further characterized by having at least five RAPD or two RPLP bands in common with strain 93-2742 or AA-0028 that are not present as corresponding RAPD or RFLP bands from strain U1.

4. The mushroom strain of claim 2, wherein said strain is further characterized by having at least one RAPD or RPLP band in common with strain U1 that is not in present as a corresponding RAPD or RPLP band from strain 93-2742 or AA-0028.

5. The mushroom strain of claim 4, wherein said strain is further characterized by having at least five RAPD or two RFLP bands in common with strain U1 that are not present as corresponding RAPD or RFLP bands from strain 93-2742 or AA-0028.

6. The mushroom strain of claim 1, wherein said strain is characterized by an RFLP marker present in strain 93-2742 as shown in Table 1.

7. The mushroom strain of claim 1, wherein said strain is characterized by an RAPD marker present in strain 93-2742 as shown in Table 2.

8. The mushroom strain of claim 1, wherein a mushroom cap of said strain has a reflectance whiteness of at least 76%.

9. The mushroom strain of claim 1, wherein a mushroom cap of said strain has a reflectance whiteness of at least 80%.

10. A method of producing white mushrooms, which comprises:

crossing an *Agaricus bisporus* mushroom strain which belongs to or is a progeny of a deposited mushroom strain identified as 93-3599, ATCC accession No. 74324, or AA-0028, ATCC accession No. 74325, or a progeny thereof with a second mushroom strain to produce a collection of crossed strains, and selecting from said crossed strains a white strain having a cap that is whiter than a U1 strain cap by a statistically significant, measurable amount.

11. The method of claim 10, wherein said white strain has a reflectance of at least 76%.

12. The method of claim 10, wherein said white strain has a reflectance of at least 80%.

13. An *Agaricus bisporus* mushroom of strain 93-3599, ATCC accession No. 74324, or a progeny thereof having all the characteristics of said strain.

14. A crossbred *Agaricus bisporus* mushroom strain being an F1 cross between 93-3599, ATCC accession No. 74324, and strain U1B, ATCC accession No. 74323, or a progeny thereof.

15. The crossbred strain of claim 14, wherein said crossbred strain contains at least one RAPD or RFLP band in common with strain 93-3599 that is not present as a corresponding RAPD or RFLP band from strain U1.

16. A progeny of the crossbred strain of claim 14 having all the characteristics said crossbred strain.

* * * * *